United States Patent [19]

Wagenknecht

[11] Patent Number: 4,978,350
[45] Date of Patent: Dec. 18, 1990

[54] TRANSCUTANEOUS PIN FOR FIXATION OF A BONE PART OR FRAGMENT

[75] Inventor: Marcel H. Wagenknecht, Le Lignon, Switzerland

[73] Assignee: Jaquet Orthopédie S.A., Geneva, Switzerland

[21] Appl. No.: 467,289

[22] Filed: Jan. 23, 1990

Related U.S. Application Data

[63] Continuation of Ser. No. 147,039, Jan. 20, 1988, abandoned, which is a continuation of Ser. No. 935,415, Nov. 26, 1986, abandoned.

[51] Int. Cl.$^5$ .............................................. A61F 5/04
[52] U.S. Cl. ...................................... 606/72; 606/73; 606/80
[58] Field of Search ................... 606/54, 65, 72, 73, 606/80

[56] References Cited

U.S. PATENT DOCUMENTS

| | | | |
|---|---|---|---|
| 1,923,177 | 8/1933 | Tucker | 128/310 |
| 2,388,482 | 1/1943 | Haynes | 128/92 YE |
| 2,532,296 | 12/1950 | Giesen | 128/92 YF |
| 4,414,966 | 11/1983 | Stednitz | 128/92 YE |
| 4,537,185 | 8/1985 | Stednitz | 128/92 YE |
| 4,541,422 | 9/1985 | de Zbikowski | 128/ZW |
| 4,612,921 | 9/1986 | de Zbikowski | 128/92 YF |
| 4,640,271 | 2/1987 | Lower | 128/92 YF |

OTHER PUBLICATIONS

Richards Technical Publication No. 4167, "Bone Screw Technical Information," 1980, pp. 1-14.

Primary Examiner—Robert A. Hafer
Assistant Examiner—Charles H. Sam
Attorney, Agent, or Firm—Peter C. Richardson; Lawrence C. Akers; Elizabeth O. Slade

[57] ABSTRACT

A transcutaneous fixation pin includes a threaded portion with flutes evenly spaced over the circumference of the pin at the anterior end of the threaded portion so as to perform a tapping operation when the end of the threaded portion penetrates a bone fragment. The flutes take the form of a notch creating a cutting edge of the tap, with clearance relief being provided behind the cutting edge of the tap which approaches the centerline of the pin until it reaches the next notch, so as to form a clearance angle. In a modification the flutes are disposed helicoidally in relation to the axis of the thread, with the helix and the thread being pitched in the same direction.

13 Claims, 2 Drawing Sheets

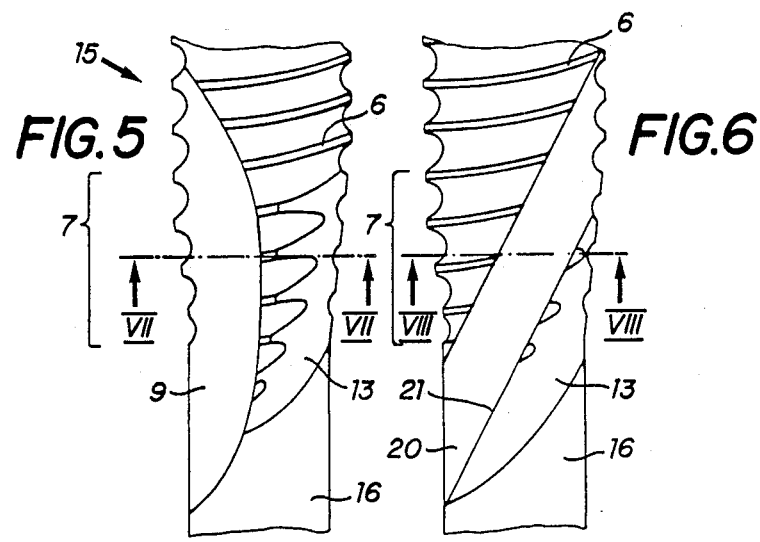
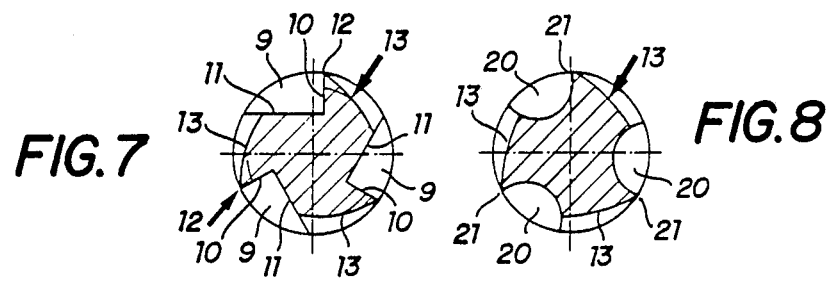
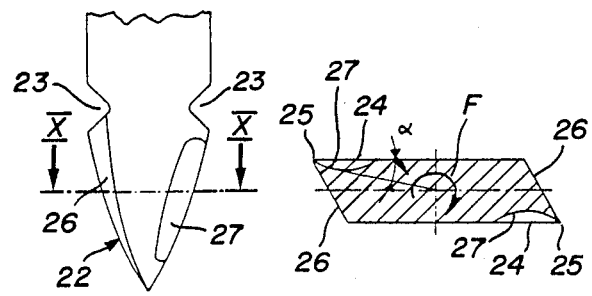

TRANSCUTANEOUS PIN FOR FIXATION OF A BONE PART OR FRAGMENT

Continuation of Ser No. 147,039, Jan. 20, 1988, abandoned, which is a continuation of application Ser. No. 06/935,415 filed on Nov. 26, 1986, now abandoned.

BACKGROUND OF THE INVENTION

Transcutaneous pins have been known for many years and are used in bone surgery, particularly in external osteosynthesis. Such pins pass through the flesh and bone and, in general, are used with the type of external skeletal fixation appliances developed by Dr. Hoffmann. These external skeletal fixation appliances comprise swivel joints, connecting bars, sliding bars, articulations, and anchorage clamps intended to hold and position the transcutaneous pins. The Hoffmann external fixation devices comprise an assembly framework placed around a part or member of the human body and arranged to hold bones or bone fragments in place from the exterior with the aid of pins or groups of transcutaneous pins.

There are many types of transcutaneous pins on the market today. These pins generally comprise a threaded portion with a tapping portion at the end arranged to cut a thread when it is screwed into a bone part or fragment. Before the pin is installed, the bone or bone fragment is first drilled to the desired diameter, which is substantially equal to or greater than the inner diameter of the thread. The end of the pin is then inserted in the drilled hole and the threaded portion of the pin is screwed into the hole. During this operation, the tap provided at the end of the pin cuts the thread in the previously drilled hole. To screw the pin into the hole, use is commonly made of a chuck engaging a portion of polygonal cross section, for example a square cross section located at one end of the pin. In the pins of the prior art, the end of the threaded portion might take a form like the point of a drilling bit or take different configurations known to those skilled in the art.

There is also a type of pin, known as a transfixing pin, in which the threaded portion is preceded by a rod having a drill tip at its free end. Transfixing pins may be installed without previously drilling a hole in the bone. In the case of a transfixing pin, the hole is drilled by the extremity of the tip and the thread is tapped by a tapping portion provided at the beginning of the thread.

The transcutaneous pins of the prior art do not afford a drilling or a tapping of very high quality. As in any drilling or tapping operation, the temperature rises at the place of the operation, which can cause necroses and deteriorations in the bone tissues. Moreover, the prior art pins do not produce tapped surfaces of good quality. The surfaces are torn out in places, thus failing to provide a good quality of anchorage between the bone fragment and the pin when the latter has been installed. Finally, the prior art pins, by reason of their poor performance in the drilling or tapping operation, can cause undue stresses in the bone when they are in place.

SUMMARY OF THE INVENTION

An object of the present invention is to propose a transcutaneous pin assuring a drilling or a tapping of good quality, while ensuring a minimal temperature rise during insertion.

The transcutaneous pin for fixation of a bone part or fragment according to the invention, comprising a threaded portion with at least one flute at the anterior end thereof adapted to perform a tapping operation when said end of the threaded portion penetrates the bone part or fragment, is characterized in that the at least one flute takes the form of notches creating a cutting edge of the tap across the threading, with a clearance relief being provided behind the cutting edge of the tap which approaches the centerline of the pin until it reaches the following notch, thereby forming a clearance angle.

The presence of the clearance relief permits a tapping of good quality and an easier penetration of the pin into the bone. Furthermore, since the chips do not remain inside the bone during the procedure and thus present no obstacle to the following cutting edge, the temperature rise is much less than with the pins of the prior art.

The anterior portion of the threading of the pin may take the form of a leading cone, with the flutes defining the cutting edges extending over the leading cone of the threading and over the beginning of the central cylindrical portion of said threading.

Various modifications may be adopted in producing the flutes forming the cutting edges. The flutes may take the form of a notch formed by two substantially perpendicular surfaces parallel to the axis of the pin. Alternatively, the flutes may take the form of a notch disposed helicoidally in relation to the axis of the thread. In a preferred embodiment, the helix and the thread are pitched in the same direction. The fluting is preferably accomplished by grinding, after the threading with its leading cone have been made.

The invention can be adapted to various types of pins, whether pins requiring a pre-drilled hole or self-drilling pins. In the latter case, the pin advantageously is provided with a drill tip at least indirectly adjacent the beginning of the leading cone of the thread.

The invention likewise comprises a transfixing pin in which the leading cone of the thread is preceded by a rod of a diameter equal to or less than the inner diameter of the thread of the threaded portion, with said rod terminating in a flat ogive-shaped drill tip. The flat ogive-shaped tip may have two clearance cutouts placed opposite each other on its upper portion.

The flat ogive-shaped tip may have a cross section in the shape of an elongated parallelogram defining two opposed cutting surfaces, each followed by a surface forming a clearance angle, said cutting and clearance surfaces forming together a cutting edge, and the cutting surfaces having an elongated spoon-shaped depression next to the cutting edge so as to modify the cutting angle to bring it to zero or to a positive value.

DETAILED DESCRIPTION OF THE INVENTION

The accompanying drawings show, by way of example, several embodiments of the transcutaneous pin according to the invention.

In the drawings:

FIG. 5 is an enlarged view of the anterior end of the threading of a transfixing pin, in a first embodiment;

FIG. 6 is a view similar to FIG. 5, in a second embodiment;

FIG. 7 is a section view taken along the line VII—VII in FIG. 5;

FIG. 8 is a section view taken along the line VIII—VIII in FIG. 6;

FIG. 9 is an enlarged detail view of the tip of the pin of FIG. 2, as indicated by the arrow IX; and FIG. 10 is a section view taken through the tip in FIG. 9, along the line X—X.

Figure 1:
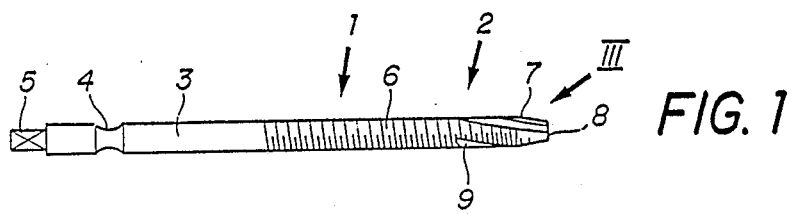
FIG. 1 is a side view showing a first embodiment of a transcutaneous pin.
Figure 3:
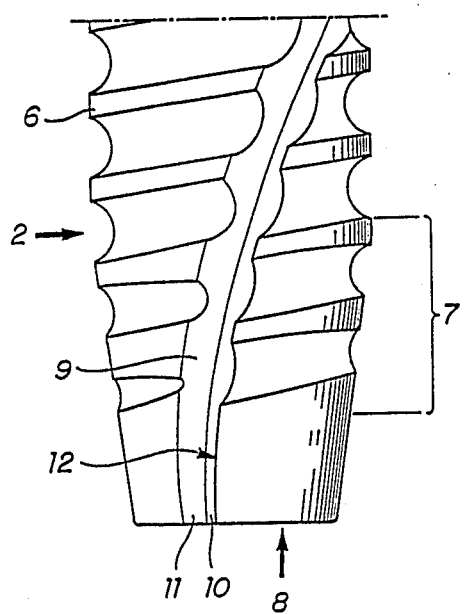
FIG. 3 is an enlarged view of the end of the pin shown in FIG. 1 as seen at III, in a first embodiment of a pin installed after the bone has been drilled to a suitable diameter; such a pin is commonly called a blunt tip half-pin.

The transcutaneous pin 1 shown in FIGS. 1 and 3 comprises a threaded portion 2, which is the anterior portion of the pin, and a posterior portion 3 which is referred to as the smooth portion 3. The pin 1 is a cylindrical pin of small diameter compared to its length, and the posterior or smooth portion 3 is provided with a groove 4 and a four-sided terminal portion 5. The terminal portion 5 enables use of a chuck to drive the pin 1 into a bone part or fragment, while the groove 4 serves for retention of the chuck. The anterior portion 2 of the pin 1 (see in particular FIG. 3) comprises a thread 6 whose anterior portion takes the form of a truncated leading cone 7 terminated by a substantially planar face 8 perpendicular to the centerline of the pin.

In FIGS. 3, 5 and 6, three flutes 9 are placed 120° apart over the circumference of the anterior end of the pin, to perform the tapping operation. These flutes 9 take the form of two perpendicular surfaces 10 and 11, with surface 10 defining the cutting edge 12 of the tap at its free end (see also the cross section of FIG. 7). Each of the cutting edges 12 is followed, in the direction of rotation of the pin, by a clearance relief 13 which approaches the centerline of the pin until it intersects the surface 11 of the following flute 9.

The flutes 9 are preferably realized by grinding. The grinding operation is performed with a circular grinder moved tangentially over the end of the thread 6. Grinding of the flutes 9 provides a good surface quality at the cutting edge and obviates a subsequent finishing operation. The clearance relief 13 is made in the same manner by bringing a grinder up to the end of the pin and rotating the latter while bringing the grinder closer to the centerline of the pin.

Although the creation of the flutes 9 and of the clearance relief by grinding has given very good results, it will be apparent to those skilled in the art that it may also be done by milling or by any other suitable means.

The type of pin shown in FIG. 3 is used more specifically to be placed in bones in such a position that, at the exit from the second cortex, the point of the pin does not risk wounding the tissues near the bone.

Figure 2:
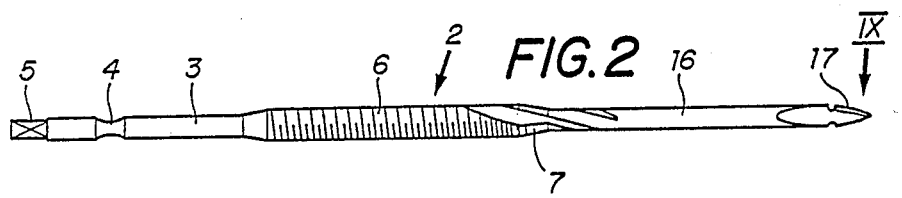
FIG. 2 is a side view showing a second embodiment of a transcutaneous pin, i.e. a transfixing pin.
Figure 4:
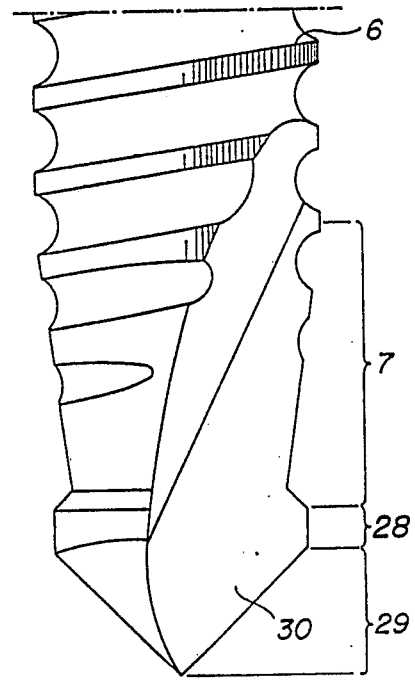
FIG. 4 is a view similar to FIG. 3 in a second embodiment of a transfixing pin serving additionally to drill the hole before making the tapping, and referred to as a self-drilling and self-tapping half-pin.

In other applications, however, it may be desirable to install a so-called transfixing pin, that is a successively self-drilling and self-tapping pin, like those shown in FIGS. 2 and 4.

In FIG. 4, as in the foregoing description, the pin includes a thread 6 terminating on a truncated conical portion 7. It nevertheless differs in that the truncated cone 7 is connected to a cylindrical portion 28 having a diameter greater than the inner diameter of the thread, which is terminated in turn by a tip 29 of generally conical shape. The cylindrical portion 28 permits avoidance of interference between the drilling and tapping operations in cortical bone of ordinary thickness, which would render difficult the correct cutting of a thread in the bone. In this embodiment, the pin includes two symmetrical flutes 30.

Alternatively, a transfixing pin such as shown in FIG. 2 may be provided, comprising, like the pin of FIG. 1, a threaded portion 2, a posterior portion 3 having an annular groove 4 adjacent its end, and a four-sided end portion 5 intended to be received by a feed chuck.

The threaded portion 2 includes a thread 6 with a leading cone 7 similar to the one detailed in FIG. 3. Here again, the tapping flutes 9 may be created by means of a circular grinder which is moved tangentially to the centerline of the pin, starting from the rod 16 preceding the truncated cone 7 and entering the threading 6. The rod 16 terminates anteriorly in a cutting tip 17 adapted to drill a hole, which is shown in more detail in FIG. 9.

The tip 17 at the end of the rod 16 of the transfixing pin shown in FIG. 2 has the shape of an ogive 22, the ogive having two clearance cutouts 23 in its upper portion (FIG. 9). The ogive-shaped tip 22 has some particularly interesting design features which are seen in FIG. 9 and in the cross section of FIG. 10 showing an elongated parallelogram configuration including two cutting surfaces 24 each defining a cutting edge 25 followed by a clearance surface 26. If the tip is rotated in the direction of rotation indicated by the arrow F, it will be noted that the surfaces 26 define a sufficiently large clearance angle to allow for the clearing of chips produced during drilling of a bone with the ogive 22. On the other hand, those skilled in the art will note in FIG. 9 that the plane surfaces 24 define cutting surfaces having a negative cutting angle alpha. In order to modify this cutting angle alpha and bring it to zero or to a positive value, two elongated depressions 27 are provided adjacent to the cutting edges 25. Thus the cutting angle alpha may be corrected and selected according to the user's preference by changing the depth of the depressions 27.

The tip of FIGS. 9 and 10, with its ogive shape, its clearance surfaces 26, and its depressions 27 bringing the cutting angle to zero or to a positive value, affords drillings of very good quality compared to prior art drill pins. The ogive-shaped tip is, moreover, especially suitable because it fixes itself in the bone and serves to drill a hole along an axis with no lateral deviation.

The pin just described with reference to FIGS. 1, 3 and 4 can vary between 75 and 200 mm in overall length, with diameters ranging from 3 to 6 mm. The truncated cone typically has an inclination of 12 degrees.

The pin according to the embodiment of FIG. 2, with a central threaded portion, may be of from 175 to 350 mm. in overall length, with diameters likewise ranging from 3 to 6 mm.. The anterior portion of the pin shown in FIG. 2, comprising the rod 16, has a diameter equal to or less than the inner diameter of the thread in the threaded portion 6. For a 3, 4, 5 or 6 mm. pin, the portion 16 may have a 2, 3, 4 and 5 mm. diameter, respectively. In the case of the pin of FIG. 2, it is advantageous to provide a 6° truncated leading cone.

In the several examples given, the threading is a single thread, but it is of course possible to alternatively provide multiple threads, the taps passing successively in the same tapping flute several times.

I claim:

1. A transcutaneous pin having a centerline and a tap, said pin for fixation of a bone part or fragment and said pin having a tap comprising a threaded portion with at least one flute at the anterior end of the threaded portion adapted to perform a tapping operation when said anterior end of the threaded portion penetrates the bone part or fragment, with the at least one flute each taking the form of a notch creating a cutting edge of the tap across the thread, and a clearance relief being provided behind the cutting edge of the tap which approaches the centerline of the pin until it reaches the following notch, thereby forming a clearance angle, wherein said at least one flute is disposed helicoidally in relation to the axis of the thread, with the helix and the thread being pitched in the same direction.

2. A pin of claim 1 including at least two flutes regularly spaced over the circumference of the pin.

3. A pin of claim 1 wherein the anterior portion of the threading takes the form of a truncated leading cone, with the flute defining the cutting edge extending over the leading cone of the threading and over the beginning of the central cylindrical portion of said threading.

4. A pin of claim 1 wherein the flute takes the form of a notch formed by two substantially perpendicular surfaces.

5. A pin of claim 1 wherein the flute takes the form of a notch having a generally rounded shape in cross section.

6. A pin of claim 1 wherein the flute has been created by grinding after the thread with its leading cone has been made.

7. A pin of claim 3 wherein the anterior portion of said truncated cone is terminated by a face perpendicular to the axis of the pin and intended to fit into a hole previously drilled in the bone part.

8. A pin of claim 3 wherein the leading code of the threading is preceded by a rod of diameter equal to or smaller than the inner thread diameter of the threaded portion, said rod terminating in a flat drill tip having the shape of an ogive.

9. A pin of claim 8 wherein the flat ogive-shaped tip has two clearance cutouts placed opposite each other on its posterior portion.

10. A pin of claim 8 wherein the flat ogive-shaped tip has a cross section in the shape of an elongated parallelogram defining two opposed cutting surfaces, each followed by a surface forming a clearance angle, said cutting and clearance surfaces forming together a cutting edge, and the cutting surfaces having an elongated spoon-shaped depression placed next to the cutting edge so as to modify the cutting angle to bring it to zero or to a positive value.

11. A pin of claim 3 wherein the anterior portion of said truncated cone is preceded, at least indirectly, by a cone including said flute or flutes so as to dorm a drill tip.

12. A pin of claim 11 wherein said leading cone is preceded by a portion of generally cylindrical shape located between the truncated leading cone and said drill cone.

13. A pin of claim 12 wherein the diameter of the cylindrical drilling portion is larger than the inner diameter of the thread.

* * * * *